United States Patent
Yoshikawa et al.

(10) Patent No.: US 9,187,502 B2
(45) Date of Patent: *Nov. 17, 2015

(54) SILICA PARTICLES AND METHOD FOR PRODUCING THE SAME

(75) Inventors: Hideaki Yoshikawa, Kanagawa (JP);
Yuka Zenitani, Kanagawa (JP);
Hiroyoshi Okuno, Kanagawa (JP);
Shunsuke Nozaki, Kanagawa (JP);
Shinichiro Kawashima, Kanagawa (JP);
Sakae Takeuchi, Kanagawa (JP)

(73) Assignee: FUJI XEROX CO., LTD., Tokyo (JP)

( * ) Notice: Subject to any disclaimer, the term of this patent is extended or adjusted under 35 U.S.C. 154(b) by 0 days.

This patent is subject to a terminal disclaimer.

(21) Appl. No.: 12/917,814

(22) Filed: Nov. 2, 2010

(65) Prior Publication Data

US 2011/0318584 A1    Dec. 29, 2011

(30) Foreign Application Priority Data

Jun. 24, 2010   (JP) .................... 2010-143828

(51) Int. Cl.
   *B32B 5/16*   (2006.01)
   *C07F 7/08*   (2006.01)
   *C07F 7/18*   (2006.01)

(52) U.S. Cl.
   CPC ............. *C07F 7/0863* (2013.01); *C07F 7/1848* (2013.01); *Y10T 428/2982* (2015.01); *Y10T 428/2993* (2015.01)

(58) Field of Classification Search
   None
   See application file for complete search history.

(56) References Cited

U.S. PATENT DOCUMENTS

| | | | |
|---|---|---|---|
| 4,775,520 A | 10/1988 | Unger et al. | |
| 4,849,390 A | 7/1989 | Sano et al. | |
| 4,902,598 A | 2/1990 | Winnik et al. | |
| 4,911,903 A | 3/1990 | Unger et al. | |
| 5,221,497 A | 6/1993 | Watanabe et al. | |
| 5,597,512 A | 1/1997 | Watanabe et al. | |
| 5,609,675 A | 3/1997 | Noritake et al. | |
| 5,674,589 A * | 10/1997 | Bennett et al. | 428/149 |
| 5,985,229 A | 11/1999 | Yamada et al. | |
| 5,998,329 A * | 12/1999 | Derolf et al. | 502/407 |
| 6,113,682 A | 9/2000 | Shin et al. | |
| 6,296,996 B1 | 10/2001 | Ogawa et al. | |
| 6,403,271 B1 | 6/2002 | Suzuki et al. | |
| 6,770,130 B2 | 8/2004 | Kato et al. | |
| 6,811,944 B2 | 11/2004 | Higuchi et al. | |
| 6,875,549 B2 | 4/2005 | Yamazaki et al. | |
| 7,846,632 B2 * | 12/2010 | Nakatani | 430/108.7 |
| 2004/0067189 A1 | 4/2004 | Sugiura et al. | |
| 2004/0137353 A1 | 7/2004 | Iida et al. | |
| 2004/0222618 A1 * | 11/2004 | Azechi et al. | 280/728.1 |
| 2004/0229040 A1 | 11/2004 | Kudo et al. | |
| 2005/0260515 A1 | 11/2005 | Kato et al. | |
| 2007/0020543 A1 | 1/2007 | Nakatani | |
| 2007/0218387 A1 * | 9/2007 | Ishii et al. | 430/108.7 |
| 2008/0086951 A1 | 4/2008 | Wakamiya et al. | |
| 2008/0268362 A1 | 10/2008 | Kudo | |
| 2009/0196658 A1 | 8/2009 | Sugiura | |
| 2010/0104323 A1 | 4/2010 | Toizumi et al. | |
| 2010/0203443 A1 | 8/2010 | Okita et al. | |
| 2010/0330488 A1 | 12/2010 | Ieda | |
| 2011/0209413 A1 | 9/2011 | Nishida et al. | |
| 2011/0318581 A1 | 12/2011 | Zenitani et al. | |
| 2011/0318584 A1 | 12/2011 | Yoshikawa et al. | |
| 2011/0319647 A1 | 12/2011 | Yoshikawa et al. | |

FOREIGN PATENT DOCUMENTS

| | | |
|---|---|---|
| CN | 86106689 A | 5/1987 |
| CN | 1202710 A | 12/1998 |
| CN | 1380585 A | 11/2002 |
| CN | 101271287 A | 9/2008 |
| CN | 101807019 A | 8/2010 |
| CN | 102295292 A | 12/2011 |
| EP | 0 574 642 A1 | 12/1993 |
| JP | A-62-52119 | 3/1987 |
| JP | A-63-310714 | 12/1988 |
| JP | A-1-317115 | 12/1989 |
| JP | A-4-187512 | 7/1992 |
| JP | A-4-238807 | 8/1992 |
| JP | A-04-255755 | 9/1992 |
| JP | A-5-4812 | 1/1993 |
| JP | A-06-041419 | 2/1994 |
| JP | A-6-254383 | 9/1994 |
| JP | A-7-118008 | 5/1995 |
| JP | A-7-277725 | 10/1995 |
| JP | A-8-12305 | 1/1996 |
| JP | A-08-283617 | 10/1996 |

(Continued)

OTHER PUBLICATIONS

Machine translation of Yamada et al. (JP 2001-189009). (dated 2001).*
Machien translation of Kasuga et al. (JP 2000-344513). (dated 2000).*
Apr. 12, 2012 Extended European Search Report issued in European Patent Application No. 11185668.8.
Sep. 10, 2012 Australian Office Action issued in Australian Patent Application No. 2011232772.
U.S. Appl. No. 13/214,816 in the name of Yoshikawa et al., filed Aug. 22, 2011.
U.S. Appl. No. 13/214,657 in the name of Zenitani et al., filed Aug. 22, 2011.

(Continued)

*Primary Examiner* — Alexandre Ferre
(74) *Attorney, Agent, or Firm* — Oliff PLC

(57) ABSTRACT

The present invention provides silica particles including primary particles, the primary particles having an average particle diameter in a range of from about 100 nm to about 500 nm, a particle size distribution index in a range of from about 1.40 to about 1.80, and an average roundness in a range of from about 0.5 to about 0.85, and about 95% or more, by number of particles, of the primary particles satisfying following Formula (1) with respect to a roundness (R) and a particle diameter (D) (nm):

$R = \alpha \times D/1000 + \beta$     Formula (1)

$(-2.5 \leq \alpha \leq -0.9, 0.8 \leq \beta \leq 1.2)$.

10 Claims, No Drawings

(56) References Cited

FOREIGN PATENT DOCUMENTS

| | | | |
|---|---|---|---|
| JP | A-09-143401 | | 6/1997 |
| JP | A-9-202612 | | 8/1997 |
| JP | A-11-60232 | | 3/1999 |
| JP | A-11-286611 | | 10/1999 |
| JP | 2000344512 A | * | 12/2000 |
| JP | A-2001-150334 | | 6/2001 |
| JP | 2001189009 A | * | 7/2001 |
| JP | 2002-029730 A | | 1/2002 |
| JP | A-2002-38049 | | 2/2002 |
| JP | A-2002-146233 | | 5/2002 |
| JP | A-2003-133267 | | 5/2003 |
| JP | A-2003-165718 | | 6/2003 |
| JP | A-2003-171117 | | 6/2003 |
| JP | A-2004-35293 | | 2/2004 |
| JP | A-2004-102236 | | 4/2004 |
| JP | A-2004-203638 | | 7/2004 |
| JP | A-2004-338969 | | 12/2004 |
| JP | A-2005-84295 | | 3/2005 |
| JP | A-2006-028319 | | 2/2006 |
| JP | A-2006-251220 | | 9/2006 |
| JP | A-2007-22827 | | 2/2007 |
| JP | A-2008-169102 | | 7/2008 |
| JP | A-2008-174430 | | 7/2008 |
| JP | A-2008-285406 | | 11/2008 |
| JP | A-2009-78935 | | 4/2009 |
| JP | A-2009-137791 | | 6/2009 |
| JP | A-2009-149493 | | 7/2009 |
| JP | A-2009-161371 | | 7/2009 |
| JP | A-2009-186512 | | 8/2009 |
| JP | A-2010-107601 | | 5/2010 |
| JP | A-2011-185998 | | 9/2011 |
| JP | A-2012-6781 | | 1/2012 |
| JP | A-2012-6789 | | 1/2012 |
| WO | WO 2008/018966 A2 | | 2/2008 |
| WO | WO 2010/052945 A1 | | 5/2010 |

OTHER PUBLICATIONS

U.S. Appl. No. 12/912,057 in the name of Zenitani et al., filed Oct. 26, 2010.
Oct. 23, 2012 Office Action issued in U.S. Appl. No. 12/912,057.
Aug. 16, 2013 Office Action issued in U.S. Appl. No. 13/214,816.
Oct. 15, 2013 Office Action issued in Japanese Application No. 2010-143828 (with English Translation).
Kim et al., "Influence of reaction conditions on sol-precipitation process producing silicon oxide particles," Ceramics International, vol. 28 (2002), pp. 187-194.
Wang et al., "Preparation of spherical silica particles by Stöber process with high concentration of tetra-ethyl-orthosilicate," Journal of Colloid and Interface Science, vol. 341, pp. 23-29, available online Sep. 18, 2009.
Nagao et al., "Particle formation in the hydrolysis of tetraethyl orthosilicate in pH buffer solution," Journal of Colloid and Interface Science, vol. 279 (2004), pp. 143-149.
Jan. 30, 2014 Office Action issued in U.S. Appl. No. 13/214,816.
Jan. 30, 2014 Office Action issued in U.S. Appl. No. 13/214,657.
Mar. 14, 2013 Office Action issued in U.S. Appl. No. 12/912,057.
Japanese Patent Office, Notice of Reasons for Rejection mailed Oct. 29, 2013 in Japanese Patent Application No. 2010-145221 w/English-language Translation.
Jul. 19, 2013 Office Action issued in U.S. Appl. No. 13/214,657.
Dec. 19, 2013 Office Action issued in Chinese Application No. 201010546805.8 (with English Translation).
Aug. 11, 2014 Notice of Information Offer issued in Japanese Patent Application No. 2011-010052 w/translation.
Jul. 22, 2013 Office Action issued in Australian Patent Application No. 2012258292.
U.S. Appl. No. 13/934,928 in the name of Iwanaga et al., filed Jul. 3, 2013.
U.S. Appl. No. 13/670,040 in the name of Iwanaga et al., filed Nov. 6, 2012.
May 23, 2014 Notice of Allowance issued in U.S. Appl. No. 12/912,057.
Mar. 21, 2014 Office Action issued in U.S. Appl. No. 13/670,040.
Aug. 20, 2014 Office Action issued in Chinese Application No. 201010546805.8 (with English Translation).
Aug. 28, 2014 Office Action issued in U.S. Appl. No. 13/670,040.
Other Document 1: Table to confirm that the oxide particles described in [Table 1] of [0265] of Publication 1 satisfy the formula (1) of Claim 1 of the present application (with English Translation).
Jul. 7, 2014 Information Offer Form issued in Japanese Application No. 2011-008842 (with English Translation).
Jan. 7, 2015 Office Action issued in U.S. Appl. No. 13/934,928.
Feb. 2, 2015 Office Action issued in Chinese Application No. 201110318138.2.
Feb. 10, 2015 Office Action issued in Chinese Application No. 201110318210.1.
Jul. 2, 2015 Office Action issued in U.S. Appl. No. 13/934,928.

* cited by examiner

SILICA PARTICLES AND METHOD FOR PRODUCING THE SAME

CROSS-REFERENCE TO RELATED APPLICATION

This application is based on and claims priority under 35 USC 119 from Japanese Patent Application No. 2010-143828 filed Jun. 24, 2010.

BACKGROUND

1. Technical Field

The present invention relates to silica particles and a method for producing the same.

2. Related Art

Silica particles are used as an added component or a main component of toners, cosmetics, rubbers, abrasives, and the like, and play a role in, for example, improvement of the strength of resins, improvement of flowability of powders, inhibition of packing, and the like. Since it is thought that the properties that silica particles have are likely to depend on the shapes of the silica particles, various shapes of silica particles have been proposed.

SUMMARY

According to an aspect of the invention, silica particles including primary particles, the primary particles having an average particle diameter in a range of from about 100 nm to about 500 nm, a particle size distribution index in a range of from about 1.40 to about 1.80, and an average roundness in a range of from about 0.5 to about 0.85, and about 95% or more, by number of particles, of the primary particles satisfying following Formula (1) with respect to a roundness (R) and a particle diameter (D) (nm):

$$R = \alpha \times D/1000 + \beta \quad \text{Formula (1)}$$

$(-2.5 \leq \alpha \leq -0.9, 0.8 \leq \beta \leq 1.2)$, are provided.

DETAILED DESCRIPTION

Exemplary embodiments according to the aspect of the invention include, but are not limited to the following items <1> to <14>.

<1> Silica particles including primary particles, the primary particles having an average particle diameter in a range of from about 100 nm to about 500 nm, a particle size distribution index in a range of from about 1.40 to about 1.80, and an average roundness in a range of from about 0.5 to about 0.85, and about 95% or more, by number of particles, of the primary particles satisfying following Formula (1) with respect to a roundness (R) and a particle diameter (D) (nm):

$$R = \alpha \times D/1000 + \beta \quad \text{Formula (1)}$$

$(-2.5 \leq \alpha \leq -0.9, 0.8 \leq \beta \leq 1.2)$.

<2> The silica particles according to the item <1>, wherein a surface of the silica particle is hydrophobized.

<3> The silica particles according to the item <2>, wherein at least a part of the surface of the silica particles includes an alkyl group.

<4> The silica particles according to the item <2>, wherein the surface of the silica particles that is hydrophobized is hydrophobized with an organosilicon compound including an alkyl group.

<5> The silica particles according to the item <4>, wherein the organic silicon compound is at least one selected from the group consisting of a silazane compound and a silane compound.

<6> The silica particles according to the item <4> or the item <5>, wherein the organosilicon compound includes trimethylsilyl group.

<7> The silica particles according to the item <6>, wherein the o organic silicon compound having trimethylsilyl group includes a trimethylmethoxysilane or a hexamethyldisilazane.

<8> The silica particles according to any one of the items <4> to <7>, wherein an added amount of the organosilicon compound is in a range of from about 1% by weight to about 100% by weight with respect to an amount of the silica particles.

<9> A method for producing the silica particles according to any one of the items <1> to <8>, the method including: providing an alkali catalyst solution, which includes a first alkali catalyst at a concentration of from about 0.6 mol/L to about 0.85 mol/L, in a solvent including an alcohol; and supplying tetraalkoxysilane and a second alkali catalyst to the alkali catalyst solution; the tetraalkoxysilane being supplied at a supply rate of from about 0.006 mol/(mol·min) to about 0.009 mol/(mol·min) with respect to 1 mol of the alcohol in the alkali catalyst solution; and the second alkali catalyst being supplied in an amount of from about 0.1 mol to about 0.4 mol per minute with respect to 1 mol of a total supply amount of the tetraalkoxysilane supplied per minute.

<10> The method for producing the silica particles according to the item <9>, wherein the solvent containing the alcohol is an alcohol or a mixed solvent including the alcohol and at least one solvent selected from the group consisting of water, ketones, cellosolves (ethylene glycol monoethers), cellosolve esters (monoesters of ethylene glycol monoethers), and ethers.

<11> The method for producing the silica particles according to the item <10>, wherein an amount of the alcohol with respect to the at least one solvent is about 80% by weight or more.

<12> The method for producing the silica particles according to any one of the items <9> to <11>, wherein the alkali catalyst is at least one selected from the group consisting of ammonia, urea, monoamines, and a quaternary ammonium salt.

<13> The method for producing the silica particles according to any one of the items <9> to <12>, wherein the tetraalkoxysilane is at least one selected from the group consisting of tetramethoxysilane, tetraethoxysilane, tetrapropoxysilane, and tetrabutoxysilane.

<14> The method for producing the silica particles according to any one of the items <9> to <13>, wherein the supply rate of the tetraalkoxysilane with respect to an amount by mol of the alcohol in the alkali catalyst solution is from about 0.0065 mol/(mol·min) to about 0.0085 mol/(mol·min).

<Silica Particles>

For the silica particles according to the present embodiment, 95% or more, by number of particles, of the primary particles having an average particle diameter from 100 nm or about 100 nm to 500 nm or about 500 nm and a particle size distribution index from 1.40 or about 1.40 to 1.80 or about 1.80 with an average roundness (circularity) from 0.5 or about 0.5 to 0.85 or about 0.85 satisfy the following formula (1) with respect to the roundness (R) (degree of circularity) and the particle diameter (D) (nm).

$$R = \alpha \times D/1000 + \beta \quad \text{Formula (1)}$$

$(-2.5 \leq \alpha \leq -0.9, 0.8 \leq \beta \leq 1.2)$

Furthermore, the above-described roundness (R) (circularity) indicates the spherical degree of a silica particle, and thus, a roundness of 1 indicates that the particle has sphericity. For the silica particles according to the present embodiment, the shape of the primary particle has an average roundness of 0.85 or less, and has more convexity and concavity than sphericity.

Hereinafter, a shape having a roundness of 0.85 or less is referred to as an "irregular shape", whereas a shape having a roundness of more than 0.85 is referred to as a "spherical shape" in some cases. That is, the shape of the silica particles according to the present embodiment is an irregular shape.

By configuring providing the silica particles according to the present embodiment as the above-described manner, the silica particles are not easily embedded in an object to be adhered. For this reason, for example, when resin particles are coated with the silica particles according to the present embodiment, and even when a load is given to the silica particles, the irregular shape can be maintained and adherence to the resin particles maintained. Although it is not clear why the silica particles according to the present embodiment are not easily embedded on an object to be adhered is not clear, it is considered to be due to the following reasons.

Note that the "primary particles" indicates the primary particles of the silica particles in the following description.

The silica particles according to the present embodiment are silica particles characterized in that the primary particles having irregular shapes with a predetermined average particle diameter have reduction in the roundness along with increase in the average particle diameter as well as a particle size distribution with a broad distribution width (the formula (1)).

That is, the silica particles according to the present embodiment are silica particles having a broad distribution width ranging from primary particles having a small particle diameter and a high roundness to primary particles having a large particle diameter and a low roundness.

Here, there is a tendency that as the particle diameter of the silica particle increases, the fluidity becomes better, whereas as the particle diameter of the silica particle decreases, the fluidity becomes worse. On the other hand, as the roundness of the silica particle increases, the fluidity becomes better, whereas as the roundness of the silica particle decreases, the fluidity becomes worse.

For this reason, it is thought that since the silica particles according to the present embodiment have the above-described broad distribution width, the fluidity is secured while maintaining the irregular shapes in the group of particles as a whole, and it is also thought that when the silica particles are adhered to an object to be adhered, even when a mechanical load from the outside is applied, the fluidity disperses the load of the silica particles on the object to be adhered.

From the above description, it is thought that the silica particles according to the present embodiment can be rendered as silica particles with irregular shapes, which are not easily embedded in an object to be adhered.

Furthermore, it is thought that since the silica particles according to the present embodiment have fluidity, they are also excellent in dispersibility on an object to be adhered or in a mixing ability when mixed with the object to be adhered.

Hereinbelow, the silica particles of the present embodiment will be described in detail.

[Physical Properties]

—Average Particle Diameter—

The silica particles of the present embodiment have an average particle diameter of the primary particles from 100 nm or about 100 nm to 500 nm or about 500 nm.

If the average particle diameter of the primary particles is less than 100 nm or about 100 nm, the shape of the particle is likely to be spherical and cannot be rendered in a shape having a roundness from 0.5 or about 0.5 to 0.85 or about 0.85. Further, when the silica particles are coated onto an object to be adhered, such as resin particles, iron powders, and the like, they are not easily dispersed on the surface of the object to be adhered. If the average particle diameter of the primary particles is more than 500 nm or about 500 nm, there may be defects when a mechanical load is given to the silica particles. Further, when the silica particles are coated on an object to be adhered, it is difficult to improve the strength of the object to be adhered and enhance the fluidity of the object to be adhered, on which the silica particles are adhered.

The average particle diameter of the primary particles is preferably from 100 nm to 350 nm, and more preferably from 100 nm to 250 nm.

The average particle diameter of the primary particles of the silica particles means a 50% diameter (D50v) in a cumulative frequency of the circle-equivalent diameters, which is obtained by observing 100 primary particles after dispersing the silica particles in the resin particles (polyester, weight average molecular weight Mw=50000) having a particle diameter of 100 μm by means of an SEM (Scanning Electron Microscope) device, and then conducting the image analysis of the primary particles.

—Particle Size Distribution Index—

The silica particles of the present embodiment have a particle size distribution index of the primary particles from 1.4 to 1.8.

If the particle size distribution index of the primary particles is less than 1.40, the particles are relatively monodisperse, and thus, have a bias to either fluidity or inhibition of embedment in an object to be adhered and there is a difficulty in satisfying both of the characteristics. If the particle size distribution index of the primary particles is more than 1.80, crude particles are generated or dispersibility in an object to be adhered is deteriorated due to a severe difference in the particle diameters, which is thus not preferable.

The particle size distribution index of the primary particles is preferably from 1.45 to 1.75.

The particle size distribution index of the primary particles of the silica particles means a square root of a value obtained by dividing the 84% diameter with the 16% diameter with respect to a cumulative frequency of the circle-equivalent diameters, which is obtained by observing 100 primary particles after dispersing the silica particles in the resin particles (polyester, weight average molecular weight Mw=50000) having a particle diameter of 100 μm by means of an SEM device, and then conducting the image analysis of the primary particles.

—Average Roundness—

The silica particles of the present embodiment have an average roundness of the primary particles from 0.5 or about 0.5 to 0.85 or about 0.85.

If the average roundness of the primary particles is more than 0.85, the primary particles are close to sphere, and accordingly, when the silica particles are added to an object to be adhered such as resin particles, powders, and the like, mixing ability or adherence to the object to be adhered is poor and the particles are vulnerable at a mechanical load, whereby the fluidity is impaired. Through this, for example, when the silica particles and the resin particle are mixed and stirred, or after they are stored over time, the silica particles become biased and adhered to the resin particles or the like, or dissociated from the resin particles or the like. If the average roundness of the primary particles is less than 0.5, a shape having a high vertical/horizontal ratio is obtained and when a mechanical load is given to the silica particles, stress concentration occurs and defects are easily generated. Further, when the silica particles according to the present embodiment are prepared by a sol-gel method, it is difficult to prepare silica particles having an average roundness of the primary particles of less than 0.5.

The average roundness of the primary particles is preferably from 0.6 to 0.8.

Furthermore, the roundness (R) of the primary particle can be obtained as "100/SF2" calculated through the following formula (2), by observing primary particles after dispersing the silica particles in the resin particles (polyester, weight average molecular weight Mw=50000) having a particle diameter of 100 μm by means of an SEM device, and then conducting the image analysis of the primary particles obtained.

$$R=(100/SF2)=4\pi \times (A/I^2) \qquad \text{Formula (2)}$$

[in the formula (2), I represents a perimeter of the primary particle in the image and A represents a projected area of the primary particle].

The average roundness of the primary particle can be obtained as a 50% roundness in a cumulative frequency of the roundness of 100 primary particles thus obtained by means of image analysis.

—Formula (1) [Relationship between Roundness and Particle Diameter of Primary Particle]—

The silica particles of the present embodiment have a relationship that 95% or about 95% by number of the primary particles having the average particle diameter, average roundness, and particle size distribution index as described above satisfy the following formula (1) with respect to the roundness (R) and the particle diameter (D) of the primary particles.

Formula regarding Roundness and Particle Diameter:

$$R=\alpha \times D/1000+\beta \qquad \text{Formula (1)}$$

$(-2.5 \leq \alpha \leq -0.9, 0.8 \leq \beta \leq 1.2)$

In the formula (1), the roundness (R) and the particle diameter (D) are values measured by observing the primary particles after dispersing the silica particles in the 100-μm resin particles by means of an SEM device, and then conducting the image analysis thereof, and a roundness is calculated from the formula (2).

If the roundness of the primary particles is larger than a range calculated from the formula (1) with respect to the particle diameter, the primary particles have good fluidity, but are easily embedded in an object to be adhered. On the other hand, if the roundness of the primary particle is smaller than a range calculated from the formula (1) with respect to the particle diameter, the primary particles are not easily embedded in an object to be adhered, but have impaired fluidity.

α and β in the formula (1) are the values of a slope (α) and an intercept (β) of the regression linear line, respectively, when the particle diameters (D) are plotted on a coordinate axis against the roundness (R) for 100 primary particles of the silica particles. If α is below −2.5, the roundness relative to the particle diameter becomes too low and the stability of the particle shape against mechanical load is reduced, whereas if α exceeds −0.9, the roundness relative to the particle diameter becomes too high and the particles are easily embedded in an object to be adhered. Further, if β is below 0.8, the roundness relative to the particle diameter becomes too low and the stability of the particle shape against the mechanical load is reduced, whereas if β exceeds 1.2, the roundness relative to the particle diameter becomes too high and the particles are easily embedded in an object to be adhered.

α is preferably from −2 to −1 ($-2 \leq \alpha \leq -1$) and β is preferably from 0.9 to 1.1 ($0.9 \leq \beta \leq 1.1$).

The ratio of the silica particles satisfying the formula (1), which is set to 95% or about 95% or more, by number of particles, of the primary particles having the average particle diameter, average roundness, and particle size distribution index as described above, is set by taking into consideration of the yield of a product in the process for preparing the silica particles. Therefore, the ratio of the silica particles which are the primary particles having the average particle diameter, average roundness, and particle size distribution index as described above and satisfy the formula (1) is preferably high, and more preferably 99% or more, by number of particles.

[Components and Surface Treatment]

The silica particles according to the present embodiment may be either crystalline or amorphous as long as they are particles having silica, that is, $SiO_2$ as a main component. Further, they may be particles prepared using silicon compounds such as liquid glass, alkoxysilane, and the like, or particles that can be obtained by grinding quartz.

Furthermore, from the viewpoint of dispersibility of the silica particles, it is preferable that the silica particle surface be hydrophobized (hydrophobization-treated). For example, by at least a part of the surface of the silica particles including an alkyl group, the silica particles are hydrophobized (hydrophobization-treated). To achieve this, for example, the silica particles are allowed to undergo a reaction with a known organic silicon compound having an alkyl group. Details of the method for hydrophobization treatment will be described later.

The silica particles according to the present embodiment are silica particles with irregular shapes, which are not easily embedded in an object to be adhered, easily maintain the irregular shapes even when mixed with resin particles or iron powders, followed by stirring or the like, and which also have excellent fluidity with the resin particles. In this regard, the silica particles according to the present embodiment can be employed in various fields such as toners, cosmetics, abrasives, and the like.

<Method for Preparing Silica Particles>

The method for preparing the silica particles according to the present embodiment is not particularly limited as long as the silica particles obtained are those in which 95% or about 95% or more, by number of particles, of the primary particles having an average particle diameter from 100 nm or about 100 nm to 500 nm or about 500 nm, a particle size distribution index from 1.40 or about 1.40 to 1.80 or about 1.80, and an average roundness from 0.5 or about 0.5 to 0.85 or about 0.85 satisfy the formula (1) with respect to the roundness and the particle diameter (nm).

For example, the silica particles according to the present embodiment may be obtained by a dry method in which silica particles having a particle diameter of more than 500 nm or about 500 nm are crushed and classified, or the silica particles may be prepared by a so-called wet method in which particles are produced by a sol-gel method using a silicon compound typically including alkoxysilane as a raw material. Examples of the wet method include a method in which a silica sol is obtained by using liquid glass as a raw material, in addition to the sol-gel method.

The silica particles according to the present embodiment are silica particles, in which 95% or about 95% or more, by number of particles, of the primary particles having an average particle diameter from 100 nm or about 100 nm to 500 nm or about 500 nm, a particle size distribution index from 1.40 or about 1.40 to 1.80 or about 1.80, and an average roundness from 0.5 or about 0.5 to 0.85 or about 0.85 satisfy the formula (1) with respect to the roundness and the particle diameter (nm), and thus, in order to prepare silica particles having various physical properties as above, it is preferable to use the method including the following steps, for preparing the silica particles according to the present embodiment.

The method for preparing the silica particles according to the present embodiment has a step of preparing an alkali catalyst solution which contains an alkali catalyst (first alkali catalyst) at a concentration from 0.6 mol/L or about 0.6 mol/L to 0.85 mol/L or about 0.85 mol/L in a solvent containing an alcohol, and a step of supplying tetraalkoxysilane at a supply amount from 0.006 mol/(mol·min) or about 0.006 mol/(mol·min) to 0.009 mol/(mol·min) or about 0.009 mol/(mol·min) relative to the alcohol in the alkali catalyst solution, and at the same time, supplying an alkali catalyst (second alkali catalyst) in an amount from 0.1 mol or about 0.1 mol to 0.4 mol or about 0.4 mol based on 1 mol of the total supply amount of tetraalkoxysilane to be supplied per minute.

That is, the method for preparing the silica particles according to the present embodiment is a method for producing silica particles by supplying an alkali catalyst as a catalyst, in addition to tetraalkoxysilane as a raw material, under the above relationship, in the presence of an alcohol including an alkali catalyst at the above-described concentration, and allowing tetraalkoxysilane to undergo a reaction therewith.

In the method for preparing the silica particles according to the present embodiment, generation of crude aggregates is low and silica particles with irregular shapes can be obtained by the above manners. The reason is not clear, but it is considered to be due to the following reasons.

First, an alkali catalyst solution containing an alkali catalyst in the solvent containing an alcohol is prepared, tetraalkoxysilane and an alkali catalyst are supplied respectively to a solution, and tetraalkoxysilane supplied to the alkali catalyst solution is allowed to undergo a reaction, thereby producing nuclear particles. In this case, it is thought that if the concentration of the alkali catalyst in the alkali catalyst solution is in the above-described range, nuclear particles with irregular shapes are produced while generation of crude aggregates such as secondary aggregates and the like is inhibited. This is because it is thought that the alkali catalyst is coordinated on the surface of the resulting nuclear particle in addition to the catalytic action, and contributes to the shape and dispersion stability of the nuclear particle, but if the amount is in the above-described range, the alkali catalyst does not cover the surface of the nuclear particle uniformly (that is, the alkali catalyst is biased and adhered on the surface of the nuclear particle), and thus, the dispersion stability of the nuclear particle is maintained, but there occurs a partial bias in the surface tension and chemical affinity in the nuclear particle, and therefore, the nuclear particles with irregular shapes are produced.

Moreover, if tetraalkoxysilane and the alkali catalyst are continuously supplied respectively, the resulting nuclear particles grow due to the reaction of tetraalkoxysilane, thereby obtaining silica particles. Here, it is thought that by carrying out the supply of tetraalkoxysilane and the alkali catalyst while maintaining the above-described relationship with respect to their supply amounts, nuclear particles with irregular shapes grow while inhibiting the production of crude aggregates such as secondary aggregates and the like and maintaining their irregular shapes, and as a result, silica particles with irregular shapes are produced. This is because it is thought that by allowing the supply amounts of tetraalkoxysilane and the alkali catalyst to satisfy the above-described relationship, the dispersion of the nuclear particles is maintained and a partial bias in the tension and the chemical affinity on the nuclear particle surface is also maintained, and as a result, particle growth of the nuclear particles occurs while maintaining the irregular shapes.

Here, it is thought that the supply amount of tetraalkoxysilane is related with the particle size distribution or roundness of the silica particles. It is thought that by setting the supply amount of the tetraalkoxysilane from 0.006 mol/(mol·min) or about 0.006 mol/(mol·min) to 0.009 mol/(mol·min) or about 0.009 mol/(mol·min), the probability of the contact between tetraalkoxysilane and the nuclear particles in the particle growth step can be increased, before tetraalkoxysilane is supplied to the nuclear particles without bias, thereby causing a reaction between tetraalkoxysilane and the nuclear particles. That is, it is thought that there is a bias in the reaction between tetraalkoxysilane and the nuclear particles. Therefore, it is thought that when bias in supplying tetraalkoxysilane to the nuclear particles is promoted, this leads to unevenness in the particle growth. Accordingly, it is assumed that the particle diameter and the shape distribution of the silica particles are increased.

Accordingly, it is thought that by setting the supply amount of tetraalkoxysilane in the above-described range, primary particles with irregular shapes, which satisfy the formula (1) and have a particle size distribution index from 1.40 or about 1.40 to 1.80 or about 1.80 and an average roundness from 0.5 or about 0.5 to 0.85 or about 0.85, are easily produced.

Further, it is thought that the average particle diameter of the silica particles depends on the total supply amount of tetraalkoxysilane.

From the above, using the method for preparing the silica particles according to the present embodiment, the crude aggregates are less generated and the silica particles with irregular shapes, which satisfy the formula (1) and have a particle size distribution index from 1.40 or about 1.40 to 1.80 or about 1.80 and an average roundness from 0.5 or about 0.5 to 0.85 or about 0.85, can be obtained.

Further, it is thought that since the nuclear particles with irregular shapes are produced by the method for preparing the silica particles according to the present embodiment, the nuclear particles grow while maintaining the irregular shapes, and thus, it is possible to produce silica particles, and as a result, silica particles with irregular shapes having high shape stability against a mechanical load can be obtained.

Moreover, it is thought that in the method for preparing the silica particles according to the present embodiment, the resulting nuclear particles with irregular shapes can grow while maintaining the irregular shapes, thereby obtaining silica particles, and accordingly, it is also thought that silica particles having strong tolerance against a mechanical load and being less susceptible to damage can be obtained.

Further, in the method for preparing the silica particles according to the present embodiment, since tetraalkoxysilane and an alkali catalyst are supplied respectively into an alkali catalyst solution and tetraalkoxysilane is allowed to undergo a reaction, thereby producing particles, the total amount of the alkali catalyst to be used is reduced, as compared with preparation of silica particles with irregular shapes by a conventional sol-gel method, and as a result, omission of a step of removing the alkali catalyst is realized. This is advantageous, particularly when the silica particles are employed in a product requiring high purity.

First, a step of preparing an alkali catalyst solution is described.

The step of preparing an alkali catalyst solution involves preparing a solvent containing an alcohol and adding an alkali catalyst thereto, thereby preparing an alkali catalyst solution.

The solvent containing an alcohol may be a solvent of an alcohol alone, or if necessary, a mixed solvent with another solvent, such as water, ketones such as acetone, methyl ethyl ketone, methyl isobutyl ketone, and the like, cellosolves (ethylene glycol monoethers) such as methyl cellosolve, ethyl cellosolve, butyl cellosolve, cellosolve esters (monoesters of ethylene glycol monoethers) such as cellosolve acetate, and the like, ethers such as dioxane, tetrahydrofuran, and the like, and others. In the case of the mixed solvent, the amount of the alcohol relative to the other solvent is desirably 80% or about 80% by weight or more (preferably 90% by weight or more).

Furthermore, examples of the alcohol include lower alcohols such as methanol, ethanol, and the like.

On the other hand, the alkali catalyst is a catalyst for promoting the reaction of tetraalkoxysilane (a hydrolysis reaction or a condensation reaction), and examples thereof include basic catalysts such as ammonia, urea, monoamines, a quaternary ammonium salt, and the like, and ammonia is particularly preferred.

The concentration (content) of the alkali catalyst is from 0.6 mol/L or about 0.6 mol/L to 0.85 mol/L or about 0.85 mol/L, preferably from 0.63 mol/L to 0.78 mol/L, and more preferably from 0.66 mol/L to 0.75 mol/L.

If the concentration of the alkali catalyst is less than 0.6 mol/L, the dispersibility of the nuclear particles in the process in which the resulting nuclear particles grow may become unstable, and crude aggregates such as secondary aggregates and the like may be produced or may be gelled, leading to deterioration of the particle size distribution in some cases.

On the other hand, if the concentration of the alkali catalyst is more than 0.85 mol/L, the stability of the resulting nuclear particle becomes excessive, spherical nuclear particles are produced and nuclear particles with irregular shapes, having an average roundness of 0.85 or less cannot be obtained, and as a result, silica particles with irregular shapes cannot be obtained.

Further, the concentration of the alkali catalyst is a concentration relative to the alcohol catalyst solution (the alkali catalyst+the solvent containing an alcohol).

Next, the particle-producing step is described.

The particle-producing step is a step in which tetraalkoxysilane and an alkali catalyst are supplied respectively to the alkali catalyst solution, and tetraalkoxysilane is allowed to undergo a reaction (a hydrolysis reaction or a condensation reaction) in the alkali catalyst solution, thereby producing silica particles.

In this particle-producing step, at an initial stage of supplying tetraalkoxysilane, nuclear particles are produced by the reaction of tetraalkoxysilane (a nuclear particle-producing step), and then nuclear particles grow (a nuclear particle growth step), thereby producing silica particles.

Examples of tetraalkoxysilane to be supplied into the alkali catalyst solution include tetramethoxysilane, tetraethoxysilane, tetrapropoxysilane, tetrabutoxysilane, and the like, but from the viewpoint of controllability of the reaction rate or the shape, the particle diameter, the particle size distribution, or the like of the silica particles obtained, tetramethoxysilane and tetraethoxysilane are preferred.

The supply amount of tetraalkoxysilane is from 0.006 mol/(mol·min) or about 0.006 mol/(mol·min) to 0.009 mol/(mol·min) or about 0.009 mol/(mol·min), relative to the alcohol in the alkali catalyst solution.

This means that tetraalkoxysilane is supplied in a supply amount from 0.006 mol or about 0.006 mol to 0.009 mol or about 0.009 mol per minute with respect to 1 mol of the alcohol used in the step of preparing an alkali catalyst solution.

By setting the supply amount of tetraalkoxysilane in the above-described range, silica particles with irregular shapes, which satisfy the formula (1) and have a particle size distribution index of the primary particles from 1.40 or about 1.40 to 1.80 or about 1.80 and an average roundness from 0.5 or about 0.5 to 0.85 or about 0.85, are easily produced at a high ratio (for example, 95% or about 95% or more by number of particles).

Furthermore, the particle diameter of the silica particles depends on the kind of tetraalkoxysilane or the reaction conditions, but by setting the total supply amount of tetraalkoxysilane used in the reaction for producing particles to, for example, 1.08 mol or more based on 1 L of the silica particle dispersion, primary particles having a particle diameter of 100 nm or more can be obtained, and by setting the total supply amount of tetraalkoxysilane used in the reaction for producing particles to 5.49 mol or less based on 1 L of the silica particle dispersion, primary particles having a particle diameter of 500 nm or less can be obtained.

It is thought that if the supply amount of tetraalkoxysilane is less than 0.006 mol/(mol·min) or about 0.006 mol/(mol·min), tetraalkoxysilane can be supplied to the nuclear particles without bias before the reaction between the nuclear particles and tetraalkoxysilane, and thus, there is no bias in both of the particle diameter and the shape and silica particles with similar shapes are produced, thereby forming particles having a narrow distribution.

This is because if the supply amount of tetraalkoxysilane is more than 0.009 mol/(mol·min), the supply amount becomes excessive, relative to a reaction of tetraalkoxysilanes with each other in the nuclear particle-forming step or a reaction of tetraalkoxysilane with the nuclear particles in the particle growth, and thus, the reaction system is easily gelled, and nuclear particle formation and particle growth are suppressed.

The supply amount of tetraalkoxysilane is preferably from 0.0065 mol/(mol·min) or about 0.0065 mol/(mol·min) to 0.0085 mol/(mol·min) or about 0.0085 mol/(mol·min), and more preferably from 0.007 mol/(mol·min) to 0.008 mol/(mol·min).

On the other hand, examples of the alkali catalyst supplied into the alkali catalyst solution include those as described above. This alkali catalyst supplied may be the same as the alkali catalyst that has been contained in advance in the alkali catalyst solution or may be different therefrom, but it is preferably the same kind.

The supply amount of the alkali catalyst is from 0.1 mol or about 0.1 mol to 0.4 mol or about 0.4 mol, preferably from 0.14 mol to 0.35 mol, and more preferably from 0.18 mol to 0.30 mol, based on 1 mol of the total supply amount of tetraalkoxysilane to be supplied per minute.

If the supply amount of the alkali catalyst is less than 0.1 mol, the dispersibility of the nuclear particles in the process in which the resulting nuclear particles grow may become unstable, and crude aggregates such as secondary aggregates may be produced or may be gelled, leading to deterioration of the particle size distribution in some cases.

On the other hand, if the supply amount of the alkali catalyst is more than 0.4 mol, the stability of the resulting nuclear particles becomes excessive, and thus, even when nuclear particles with irregular shapes are produced in the nuclear particle-producing step, spherical nuclear particles grow in the nuclear particle growth step, and as a result, silica particles with irregular shapes cannot be obtained.

Here, in the particle-producing step, tetraalkoxysilane and the alkali catalyst are supplied respectively into the alkali catalyst solution, and the supply method may be a method for continuous supply or a method for intermittent supply.

Furthermore, in the particle-producing step, the temperature in the alkali catalyst solution (the temperature during supply) is preferably, for example, from 5° C. to 50° C., and preferably in the range of from 15° C. to 40° C.

Through the above-described steps, silica particles can be obtained. In this state, the silica particles are obtained in a dispersion state, but they may be used as they are as a silica particle dispersion or may be used as extracted powders of the silica particles after removal of the solvent.

When the silica particles are used as a silica particle dispersion, the solid concentration of the silica particles can be adjusted by dilution in an alcohol or by concentration, if necessary. Further, the silica particle dispersion may be used after dilution with a solvent, including water-soluble organic solvents such as alcohols, esters, ketones, and the like, and others.

On the other hand, when the silica particles are used as powders of the silica particles, it is necessary to remove the solvent from the silica particle dispersion, and examples of the method for removing the solvent include known methods such as 1) a method in which the solvent is removed by filtration, centrifugation, distillation, or the like, followed by drying using a vacuum dryer, a tray dryer, or the like, 2) a method in which a slurry is directly dried by a fluidized bed dryer, a spray drier, or the like, and others. The drying temperature is not particularly limited, but it is preferably 200° C. or lower. If it is higher than 200° C., coalescence among the primary particles due to condensation of a silanol group remaining on the silica particle surface or generation of crude particles easily occurs.

For the dried silica particles, it is preferable to remove the crude particles or aggregates by disintegrating or sieving. The disintegrating method is not particularly limited, but it is carried out, for example, by a dry grinding device such as a jet mill, a vibration mill, a ball mill, a pin mill, and the like. The sieving method is carried out, for example, by a known device such as a vibration sieve, a wind sieving machine, and the like.

The silica particles obtained by the method for preparing the silica particles according to the present embodiment may be used after the surface of the silica particles is hydrophobization-treated by a hydrophobization treatment agent.

Examples of the hydrophobization treatment agent include known organic silicon compounds having an alkyl group (for example, a methyl group, an ethyl group, a propyl group, a butyl group, and the like), and specific examples thereof include, for example, a silazane compound such as hexamethyldisilazane, tetramethyldisilazane, and the like; silane compounds such as methyltrimethoxysilane, dimethyldimethoxysilane, trimethylchlorosilane, trimethylmethoxysilane, and the like; and others. The hydrophobization treatment agents may be used singly or in combination of plural kinds thereof.

Among these hydrophobization treatment agents, a trimethylsilyl group-containing organic silicon compound such as trimethylmethoxysilane, hexamethyldisilazane, and the like is suitable.

The amount of the hydrophobization treatment agent to be used is not particularly limited, but it is, for example, from 1% or about 1% by weight to 100% or about 100% by weight, and preferably from 5% by weight to 80% by weight, based on the silica particles, in order to attain an effect of hydrophobization.

Examples of the method for obtaining a hydrophobic silica particle dispersion which has been hydrophobization-treated by a hydrophobization treatment agent include a method in which a required amount of a hydrophobization treatment agent is added to a silica particle dispersion, and allowed to undergo a reaction at a temperature in the range from 30° C. to 80° C. under stirring to subject the silica particles to a hydrophobization treatment, thereby obtaining a hydrophobic silica particle dispersion. If the reaction temperature is lower than 30° C., the reaction for hydrophobization treatment hardly proceeds, whereas if the temperature is higher than 80° C., gelation of a dispersion by self-condensation of the hydrophobization treatment agent, aggregation among the silica particles, or the like easily occurs in some cases.

On the other hand, examples of the method for obtaining powders of the hydrophobic silica particles include a method in which the hydrophobic silica particle dispersion is obtained by the above-described method, and then dried by the above-described method to obtain powders of the hydrophobic silica particles, a method in which the silica particle dispersion is dried to obtain powders of the hydrophilic silica particles, and then hydrophobization-treated by the addition of a hydrophobization treatment agent, to obtain powders of the hydrophobic silica particles, a method in which the hydrophobic silica particle dispersion is obtained, then dried to obtain powders of the hydrophobic silica particles, and thereafter, hydrophobization-treated by the addition of a hydrophobization treatment agent, thereby obtaining powders of the hydrophobic silica particles, and the like.

Here, examples of the method for subjecting the powders of the silica particles to a hydrophobization treatment include a method in which the powders of the hydrophilic silica particles are stirred in a treatment tank such as a Henschel mixer, a fluidized bed, and the like, a hydrophobization treatment agent is added thereto, and then the inside of the treatment tank is heated to turn the hydrophobization treatment agent into a gas and allowed to undergo a reaction with a silanol group on the surface of the powders of the silica particles. The treatment temperature is not particularly limited, but it is, for example, from 80° C. to 300° C., and preferably from 120° C. to 200° C.

EXAMPLES

Hereinbelow, the present invention will be described in more detail with reference to Examples. However, the present invention is not limited to these Examples. Further, "parts" and "%" are based on weight unless otherwise specified.

Example 1

Step of Preparing Alkali Catalyst Solution
[Preparation of Alkali Catalyst Solution (1)]

In a glass-made reaction vessel with a volume of 2 L, having a stirring blade, a drop nozzle, and a thermometer, 300 g of methanol and 50 g of 10% aqueous ammonia are added and mixed under stirring to obtain an alkali catalyst solution (1). At this time, the ammonia catalyst amount of the alkali catalyst solution (1):$NH_3$ amount ($NH_3$ [mol]/($NH_3$+methanol+water) [L]) is 0.68 mol/L.

—Particle-Producing Step [Preparation of Silica Particle Suspension (1)]—

Next, the temperature of the alkali catalyst solution (1) is adjusted to 25° C., and air in the reaction vessel with the alkali catalyst solution (1) is replaced with nitrogen gas. Thereafter, 450 g of tetramethoxysilane (TMOS) and 270 g of aqueous ammonia at a catalyst ($NH_3$) concentration of 4.44% by weight are started to be added dropwise at the same time in the following supply amounts to the alkali catalyst solution (1) under stirring at 120 rpm, in which the dropwise addition is carried out over 50 minutes, thereby obtaining a suspension of the silica particles (silica particle suspension (1)).

Here, the supply amount of tetramethoxysilane (TMOS) is set to 9 g/min based on the total moles of methanol in the alkali catalyst solution (1), that is, 0.0063 mol/(mol·min). Further, the supply amount of 4.44% aqueous ammonia is set to 5.4 g/min based on the total supply amount (0.0592 mol/min) of tetraalkoxysilane to be supplied per minute. This corresponds to 0.24 mol/min based on 1 mol of the total supply amount of tetraalkoxysilane to be supplied per minute.

Thereafter, 250 g of the solvent of the silica particle suspension (1) obtained is evaporated by heating and distillation, and 250 g of pure water is added thereto, followed by drying by a lyophilizer, thereby obtaining hydrophilic silica particles (1) with irregular shapes.

—Hydrophobicization Treatment of Silica Particles—

Furthermore, 20 g of trimethylsilane is added to 100 g of the hydrophilic silica particles (1), and is allowed to undergo a reaction at 150° C. for 2 hours, thereby obtaining the hydrophobic silica particles (1) with irregular shapes, having a hydrophobization-treated silica surface.

The hydrophobic silica particles (1) obtained are added to resin particles having a particle diameter of 100 μm, and 100 primary particles of the hydrophobic silica particles (1) are subjected to SEM imaging. Then, image analysis is conducted on the SEM image obtained, and as a result, the primary particles of the hydrophobic silica particles (1) are observed to be irregular particles having an average particle diameter (D50v) of 180 nm, a particle size distribution index of 1.52, and an average roundness [100/SF2] of 0.58, and also 99 primary particles among 100 primary particles of the hydrophobic silica particles (1) which have been subjected to SEM imaging satisfies the formula (1).

For 100 primary particles of the hydrophobic silica particles (1) which have been subjected to SEM imaging, the roundness is plotted along a vertical axis and the particle diameter is plotted along a horizontal axis, and the regression line being obtained from the plotted points has α of −2.1 and β of 1.1.

Various characteristics of the hydrophobic silica particles (1) are evaluated, and as a result, the dispersibility of the primary particles is observed to be excellent, and the dispersibility, mixing ability, and adhesion when the hydrophobic silica particles (1) are dispersed in the resin particles are also observed to be excellent. In addition, the resin particles coated with the hydrophobic silica particles (1) are excellent in fluidity, the hydrophobic silica particles (1) exhibits a sufficient strength without damage against a mechanical load such as stirring, and furthermore, embedment of the hydrophobic silica particles (1) in the resin particle surface due to a mechanical load is inhibited.

Moreover, details of the method for evaluation of various characteristics of the hydrophobic silica particles (1) are as follows.

(Dispersibility of Primary Particles)

For evaluation of the primary particles of the hydrophobic silica particles (1), 0.05 g of the silica particles are added to a mixed liquid of 40 g of pure water and 1 g of methanol, the particle size distribution after performing dispersion for 10 minutes using an ultrasonic dispersing device is measured by an LS coulter (particle size measurement device, manufactured by Beckman Coulter, Inc.), and the distribution forms of the volume particle size distribution are evaluated in accordance with the following evaluation criteria.

—Evaluation Criteria—

A: A case where the peak value of the volume particle size distribution has one maximum and the dispersibility is good.

B: A case where the volume particle size distribution has two maxima, the main peak value is a 10-fold value of the other peak value, and the dispersibility is non-problematic in practical applications.

C: A case where the peak value of the volume particle size distribution has three or more maxima and the dispersibility is poor.

(Dispersibility, Fluidity, Strength, and Embedment Property in Resin Particles in Dispersion in Resin Particles)

Evaluation of each of the properties of the dispersibility, fluidity, strength, and inhibition of embedment in the resin particles of the hydrophobic silica particles (1) when being dispersed in the resin particles is carried out by each evaluation as described below, and evaluation is carried out in accordance with the following evaluation criteria.

(Dispersibility when being Dispersed in Resin)

For evaluation of the dispersibility of the hydrophobic silica particles (1) when being dispersed in the resin particles, 0.005 g of the hydrophobic silica particles (1) are added to 5 g of the resin particles having a particle diameter of 100 μm, and mixed under shaking for 10 minutes using a shaker, the resin particle surface is then observed by means of an SEM device, and evaluation is conducted in accordance with the following evaluation criteria.

—Evaluation Criteria (Dispersibility)—

A: A case where the silica particles are uniformly dispersed in the resin particle surface.

B: A case where a few aggregates of the silica particles can be seen, but reduction in the coverage on the resin particle surface cannot be seen, which is thus non-problematic in practical applications.

C: A case where scattered aggregates of the silica particles can be seen, reduction in the coverage on the resin particle surface can be seen apparently, and dispersion is poor.

(Fluidity when being Dispersed in Resin)

For evaluation of the fluidity of the hydrophobic silica particles (1) when being dispersed in the resin particles, 0.05 g of the silica particles are added to 2 g of the resin particles having a particle diameter of 10 μm, mixed under shaking for 20 minutes using a shaker, then loaded on a 75-μm sieve, and vibrated at an amplitude of 1 mm for 90 seconds, the falling type of the resin particles is observed, and evaluation is conducted in accordance with the following evaluation criteria.

—Evaluation Criteria (Fluidity)—

A: Resin particles do not remain on the sieve.

B: A few resin particles remain on the sieve.

C: Significant amount of resin particles remain on the sieve.

(Strength when being Dispersed in Resin)

For evaluation of the strength of the hydrophobic silica particles (1) when being dispersed in the resin particles, 0.005 g of the hydrophobic silica particles (1) are added to 5 g of the resin particles having a particle diameter of 100 μm (polyester, weight average molecular weight Mw=50000) and mixed under shaking for 10 minutes using a shaker, and a sample for SEM observation is collected therefrom. The collected sample is taken as a sample (1). The sample (1) is further shaken for 30 minutes using a shaker, and then the collected sample is taken as a sample (2). For each of the sample (1) and the sample (2) obtained, the circle-equivalent diameters of 100 primary particles are determined by SEM observation and image analysis, and both are compared and evaluation is carried out in accordance with the following evaluation criteria.

—Evaluation Criteria (Strength)—

A: A case where difference cannot be seen in the circle-equivalent diameters of the samples (1) and (2), and there is no defect in the silica particles.

B: A case where little reduction in the circle-equivalent diameters can be seen in the sample (2), but it is non-problematic in practical applications.

C: A case where conspicuous reduction in the circle-equivalent diameters can be seen in the sample (2), and the strength is insufficient.

(Embedment Property in Resin)

For evaluation of the embedment property in the resin of the hydrophobic silica particles (1) when being dispersed in the resin particles (evaluation as to whether the embedment is inhibited or not), 0.05 g of the hydrophobic silica particles (1) are added to 5 g of the resin particles having a particle diameter of 6 μm (polyester, weight average molecular weight Mw=50000), and shaken for 60 minutes using a shaker. Then, the embedment state of the silica particles in the resin particle surfaces is observed by SEM observation and evaluated in accordance with the following evaluation criteria.

—Evaluation Criteria (Embedment Property)—

A: A case where for the remaining silica particles, 30% by number or more are not embedded.

B: A case where for the remaining silica particles, 5% by number or more and less than 30% by number are not embedded.

C: A case where less than 5% of the silica particles are not embedded.

The preparation conditions, the physical properties, and the evaluation results of the hydrophobic silica particles (1) are shown in Tables 1 and 2.

Examples 2 to 6 and Comparative Examples 1 to 7

In the substantially same manner as that in the preparation of the alkali catalyst solution (1), except that "50 g" of 10% aqueous ammonia is changed to the amounts shown in the sections of "Component to be Added", "10% Aqueous Ammonia", and "mass (g)" in Table 1, the alkali catalyst solution (2) through the alkali catalyst solution (6), and the alkali catalyst solution (101) through the alkali catalyst solution (107) are prepared.

Each of the catalyst amount:$NH_3$ amount in the alkali catalyst solution (2) through the alkali catalyst solution (6), and the alkali catalyst solution (101) through the alkali catalyst solution (107) after preparation as described above is shown in the sections of "Component to be Added", "10% Aqueous Ammonia", and "$NH_3$ amount [mol/L]" in Table 1.

Thereafter, in the substantially same manner as that in the preparation of the silica particle suspension (1), except that the alkali catalyst solution (2) through the alkali catalyst solution (6), or the alkali catalyst solution (101) through the alkali catalyst solution (107) are used instead of the alkali catalyst solution (1), and the amount and the supply amount of tetramethoxysilane to be added to the alkali catalyst solution, and the catalyst concentration, the amount, and the supply amount of the aqueous ammonia to be added to the alkali catalyst solution are changed to the amounts shown in Table 1, attempts are made to prepare the silica particle suspension (2) to the silica particle suspension (6), and the silica particle suspension (101) to the silica particle suspension (107).

Specifically, as for the amount and the supply amount of tetramethoxysilane to be added to the alkali catalyst solution, the amount of tetramethoxysilane, "450 g", is changed to the amounts shown in the sections of "Total addition amount", "TMOS", and "mass [g]" in Table 1, and the supply amount of tetramethoxysilane, "9 g/min", is changed to the amounts shown in the sections of "Supply amount [g/min]" and "TMOS" in Table 1.

For the catalyst concentration, the amount, and the supply amount of aqueous ammonia to be added to the alkali catalyst solution, the catalyst concentration "4.44%" of aqueous ammonia is changed to the amounts shown in the sections of "Total addition amount", "Aqueous ammonia", and "$NH_3$ concentration [%]" in Table 1, and the amount of aqueous ammonia, "270 g", is changed to amounts shown in the sections of "Total addition amount", "Aqueous ammonia", and "mass [g]" in Table 1, and the supply amount of aqueous ammonia, "5.4 g/min", is changed to the amounts shown in the sections of "Supply amount [g/min]" and "Aqueous ammonia" in Table 1.

Here, the supply amounts of the ammonia catalyst to the alkali catalyst solution (2) through the alkali catalyst solution (6), and the alkali catalyst solution (101) through the alkali catalyst solution (107), which are the amounts based on 1 mol of the total supply amount of tetraalkoxysilane to be supplied per minute, are shown in the sections of "Relative amount" and "$NH_3$ amount [mol/min] (relative to TMOS)" in Table 1.

Further, the supply amounts of tetraalkoxysilane (TMOS) to the alkali catalyst solution (2) through the alkali catalyst solution (6), and the alkali catalyst solution (101) through the alkali catalyst solution (107), which are the amounts based on 1 mol of methanol in the alkali catalyst solution (2) through the alkali catalyst solution (6), and the alkali catalyst solution (101) through the alkali catalyst solution (107) are shown in the sections of "Relative amount" and "TMOS amount [mol/(mol·min)] (relative to methanol)" in Table 1.

For the silica particle suspension (2) to the silica particle suspension (6), the silica particle suspension (101) to the silica particle suspension (104), and the silica particle suspension (107), thus are obtained, the solvent is removed by distillation and dried in substantially the same manner as that for the silica particle suspension (1), to obtain the hydrophilic silica particles (2) through the hydrophilic silica particles (6), the hydrophilic silica particles (101) through the hydrophilic silica particles (104), and the hydrophilic silica particles (107).

Furthermore, for the silica particle suspension (105) of Comparative Example 5 and the silica particle suspension (106) of Comparative Example 6, the liquid phase became gelled in the particle-producing step, and thus, the hydrophilic silica particles could not be obtained.

Further, the hydrophilic silica particles (2) through the hydrophilic silica particles (5), the hydrophilic silica particles (101) through the hydrophilic silica particles (104), and the hydrophilic silica particles (107) are hydrophobization-treated as in Example 1, thereby obtaining the hydrophobic silica particles (2) through the hydrophobic silica particles (5), the hydrophobic silica particles (101) through the hydrophobic silica particles (104), and the hydrophobic silica particles (107).

The SEM images of the hydrophobic silica particles (2) through the hydrophobic silica particles (5), the hydrophobic silica particles (101) through the hydrophobic silica particles (104), the hydrophobic silica particles (107), and the hydrophilic silica particles (6), thus are obtained, are observed in substantially the same manner as that for the hydrophobic silica particles (1), and image analysis thereof are conducted. Each of the average particle diameter of the primary particles (D50v), the particle size distribution index, and the average roundness [100/SF2], being obtained by the image analysis, is shown in the section of "Primary particle characteristics" in Table 2.

Further, the distinction of hydrophobicity/hydrophilicity and the shapes of the silica particles being obtained are shown in the sections of "Primary particle characteristics" and "Hydrophobicity/Hydrophilicity and Shape" in Table 2. Hydrophobic and Irregular indicates that the silica particles are hydrophobic silica particles with irregular shape, Hydrophilic and Irregular indicates that the silica particles are hydrophilic silica particles with irregular shape, and Hydrophobic and Spherical indicates that the silica particles are hydrophobic silica particles with the spherical shapes.

For the hydrophobic silica particles (2) through the hydrophobic silica particles (5), the hydrophobic silica particles (101) through the hydrophobic silica particles (104), the hydrophobic silica particles (107), and the hydrophilic silica particles (6) being obtained, the ratio of the primary particles satisfying the formula (1) in 100 primary particles of the respective silica particles which had been subjected to SEM imaging are shown in the sections of "Primary particle characteristics", "Formula (1)", and "Ratio" in Table 2. Further, the unit of the numeral values in the section of "Ratio" is [% by number]. In addition, in the section of "Satisfactory or Unsatisfactory", a case where the ratio is 95% or about 95% by number or more is denoted as Satisfactory, whereas a case where the ratio is less than 95% or about 95% by number is denoted as Unsatisfactory.

For 100 primary particles of the respective silica particles which have been subjected to SEM imaging, the roundness is plotted along the vertical axis and the particle diameter is plotted along the horizontal axis, and α and β of a regression line obtained from the plotted points are shown in "Regression line" and the sections of "α" and "β" in Table 2.

Furthermore, various characteristics of the hydrophobic silica particles (2) through the hydrophobic silica particles (5), the hydrophobic silica particles (101) through the hydrophobic silica particles (104), the hydrophobic silica particles (107), and the hydrophilic silica particles (6) are evaluated in substantially the same manner as that for the hydrophobic silica particles (1), and the evaluation results are shown in Table 2.

TABLE 1

| | Preparation step Components to be added | | | Particle producing step | | | | | |
|---|---|---|---|---|---|---|---|---|---|
| | | 10% Aqueous ammonia | | | Total addition amount | | Supply amount [g/min] | | Supply amount [relative amount] |
| | Methanol | NH$_3$ | | TMOS | Aqueous ammonia | | | NH$_3$ amount [mol/min] | TMOS amount [mol/(mol · min)] |
| | weight [g] | weight [g] | amount [mol/L] | weight [g] | weight [g] | concentration [%] | TMOS | Aqueous ammonia | (relative to MOS) | (relative to methanol) |
| Ex. 1 | 300 | 50 | 0.68 | 450 | 270 | 4.44 | 9 | 5.4 | 0.24 | 0.0063 |
| Ex. 2 | 300 | 54 | 0.73 | 550 | 285 | 4.74 | 11 | 5.7 | 0.22 | 0.0077 |
| Ex. 3 | 300 | 56 | 0.75 | 600 | 270 | 4.44 | 12 | 5.4 | 0.18 | 0.0084 |
| Ex. 4 | 300 | 52 | 0.71 | 500 | 290 | 4.14 | 9.1 | 5.3 | 0.21 | 0.0064 |
| Ex. 5 | 300 | 49 | 0.67 | 450 | 280 | 4.64 | 9 | 5.6 | 0.26 | 0.0063 |
| Ex. 6 | 300 | 52 | 0.71 | 450 | 280 | 4.64 | 9 | 5.6 | 0.26 | 0.0063 |
| Comp. Ex. 1 | 300 | 52 | 0.71 | 450 | 270 | 4.44 | 4.5 | 2.7 | 0.24 | 0.0032 |
| Comp. Ex. 2 | 300 | 55 | 0.74 | 700 | 310 | 4.52 | 14 | 6.2 | 0.18 | 0.0098 |
| Comp. Ex. 3 | 300 | 90 | 1.12 | 500 | 330 | 7.58 | 10 | 6.6 | 0.45 | 0.007 |
| Comp. Ex. 4 | 300 | 70 | 0.91 | 500 | 310 | 7.42 | 11.1 | 6.9 | 0.41 | 0.0078 |
| Comp. Ex. 5 | 300 | 35 | 0.5 | 450 | 270 | 4.44 | 4.5 | 5.4 | 0.24 | 0.0032 |
| Comp. Ex. 6 | 300 | 45 | 0.62 | 450 | 100 | 4.44 | 9 | 2 | 0.09 | 0.0063 |
| Comp. Ex. 7 | 300 | 50 | 0.68 | 450 | 270 | 4.44 | 7.1 | 4.3 | 0.24 | 0.005 |

TABLE 2

| | Primary particle characteristics | | | | | | | Characteristics of the resulting particles | | | | |
|---|---|---|---|---|---|---|---|---|---|---|---|---|
| | Particle D50v [nm] | Average size distribution | roundness [100/SF2] | Hydrophobicity/ Hydrophilicity and Shap | Formula (1) Satisfactory or Unsatisfactory | Ratio | Regression line α | β | Disp' Prim' Part' | Properties of resin particle coating | | |
| | | | | | | | | | | Dispersibility | Fluidity | Strength | Embedment |
| Ex. 1 | 180 | 1.52 | 0.58 | Hydrophobic and Irregular | Satisfactory | 99 | −2.1 | 1.1 | A | A | A | A | A |
| Ex. 2 | 320 | 1.65 | 0.65 | Hydrophobic and Irregular | Satisfactory | 100 | −2.4 | 1 | A | A | A | A | A |
| Ex. 3 | 430 | 1.73 | 0.78 | Hydrophobic and Irregular | Satisfactory | 99 | −1.8 | 0.95 | A | A | A | A | A |
| Ex. 4 | 240 | 1.6 | 0.71 | Hydrophobic and Irregular | Satisfactory | 98 | −2 | 0.9 | A | A | A | A | A |
| Ex. 5 | 130 | 1.46 | 0.82 | Hydrophobic and Irregular | Satisfactory | 97 | −1.2 | 1.15 | A | A | A | A | A |
| Ex. 6 | 190 | 1.42 | 0.82 | Hydrophilic and Irregular | Satisfactory | 96 | −0.95 | 0.85 | B | B | A | A | A |
| Comp. Ex. 1 | 250 | 1.25 | 0.83 | Hydrophobic and Irregular | Satisfactory | 96 | −2.2 | 1 | A | A | A | A | C |
| Comp. Ex. 2 | 420 | 2.2 | 0.84 | Hydrophobic and Irregular | Unsatisfactory | 85 | −0.7 | 0.75 | C | C | B | A | A |
| Comp. Ex. 3 | 600 | 1.5 | 0.94 | Hydrophobic and Spherical | Unsatisfactory | 60 | −0.8 | 1.1 | C | B | B | A | B |
| Comp. Ex. 4 | 300 | 1.6 | 0.93 | Hydrophobic and Spherical | Unsatisfactory | 75 | −3 | 1.4 | B | B | B | A | C |
| Comp. Ex. 5 | Gel phase | — | — | — | — | — | — | — | — | — | — | — | — |

TABLE 2-continued

| | Primary particle characteristics | | | | | | | | Characteristics of the resulting particles | | | | |
|---|---|---|---|---|---|---|---|---|---|---|---|---|---|
| | D50v [mm] | Particle size distribution | Average roundness [100/SF2] | Hydrophobicity/ Hydrophilicity and Shap | Formula (1) Satisfactory or Unsatisfactory | Regression line | | | Disp' Prim' Part' | Properties of resin particle coating | | | |
| | | | | | | Ratio | α | β | | Dispersi- bility | Fluidity | Strength | Embed- ment |
| Comp. Ex. 6 | Gel phase | — | — | — | — | — | — | — | — | — | — | — | — |
| Comp. Ex. 7 | 200 | 1.3 | 0.82 | Hydrophobic and Irregular | Satisfactory | 97 | −2 | 1.1 | A | A | A | A | C |

As seen from Table 2, all of the hydrophobic silica particles (2) to (5) have irregular shapes and are excellent in strength, as for the hydrophobic silica particles (1), and even when they are dispersed in the resin particles to give a mechanical load, embedment in the resin particles is inhibited (embedment was evaluated as A). Further, they exhibits excellent dispersibility of the primary particles, and thus, the dispersibility, mixing ability, adhesion, and fluidity of the resin particles when the hydrophobic silica particles (2) to (5) are dispersed in the resin particles were excellent.

The hydrophilic silica particles (6) are not slightly superior in the dispersibility of the primary particles, and the dispersibility, mixing, and adhesion when being dispersed in the resin particles, as compared with the hydrophobic silica particles (1) to (5), but they have good fluidity when the hydrophilic silica particles (6) are dispersed in the resin particle and a sufficient strength against a mechanical load such as stirring and the like. In addition, the effect of inhibition of embedment in the resin particle surface against a mechanical load is perceived, and even as for the embedment evaluation, good results are attained.

The hydrophobic silica particles (101) have good dispersibility of the primary particles as well as good dispersibility, mixing ability, and adhesion when the hydrophobic silica particles (101) are dispersed in the resin particles. Also, they have good fluidity of the resin particles when the hydrophobic silica particles (101) are dispersed in the resin particles, and a sufficient strength against a mechanical load such as stirring and the like. However, conspicuous embedment in the resin particle surface against a mechanical load is perceived, and thus, unsatisfactory results are obtained for the embedment evaluation.

As a result of the image analysis of the silica particles, it can be seen that the hydrophobic silica particles (102) have a particle size distribution index of 2.2 and coexistence of crude contents. The average roundness of the primary particles [100/SF2] of the hydrophobic silica particles (102) is 0.84, which indicates irregular particles, but the relationship between the roundness and the particle diameter does not satisfy the formula (1).

For the hydrophobic silica particles (102), unsatisfactory results are obtained on their dispersibility of the primary particles as well as on their dispersibility, mixing ability, and adhesion when the hydrophobic silica particles (102) are dispersed in the resin particles. In addition, as for the fluidity of the resin particles to which the silica particles have been added, unsatisfactory results are obtained. On the other hand, for the embedment evaluation regarding the strength against a mechanical load such as stirring and the like, inhibition of the embedment in the resin particle surface, or the like, good results are attained.

As a result of the image analysis of the silica particles, the hydrophobic silica particles (103) are observed to be spherical particles having an average roundness [100/SF2] of 0.94. Also, the relationship between the roundness and the particle diameter does not satisfy the formula (1). The hydrophobic silica particles (104) are also spherical particles like the hydrophobic silica particles (103), and the relationship between the roundness and the particle diameter does not satisfy the formula (1).

For the hydrophobic silica particles (103) and the hydrophobic silica particles (104), unsatisfactory results are obtained for their dispersibility of the primary particles as well as on their dispersibility, mixing ability, and adhesion when the hydrophobic silica particles (103) or the hydrophobic silica particles (104) are dispersed in the resin particles, and also their fluidity with the resin particles to which the silica particles have been added. On the other hand, the strength against a mechanical load such as stirring is good, but the effect of inhibition of the embedment in the resin particle surface can not be obtained, and for the embedment evaluation, unsatisfactory results are obtained.

As described above, in Comparative Examples 5 and 6, the dispersion in the particle-producing step becomes gelled, and therefore, silica particles can not be obtained. For this reason, "-" is marked in each of the sections of Primary particle characteristics and Evaluation in Table 2.

For the hydrophobic silica particles (107), the particle size distribution index is low (1.3), the effect of inhibition of the embedment in the resin particle surface can not be obtained, and for the embedment evaluation, unsatisfactory results are obtained.

The foregoing description of the exemplary embodiments of the present invention has been provided for the purposes of illustration and description. It is not intended to be exhaustive or to limit the invention to the precise forms disclosed. Obviously, many modifications and variations will be apparent to practitioners skilled in the art. The exemplary embodiments were chosen and described in order to best explain the principles of the invention and its practical applications, thereby enabling others skilled in the art to understand the invention for various embodiments and with the various modifications as are suited to the particular use contemplated. It is intended that the scope of the invention be defined by the following claims and their equivalents.

What is claimed is:

1. Silica particles for an external additive of a toner, the silica particles comprising:
   the primary particles having:
      an average particle diameter in a range of from about 130 nm to about 430 nm,
      a particle size distribution index in a range of from about 1.52 to about 1.75, where the particle distribution index means a square root of a value obtained by dividing a 84% diameter with a 16% diameter with respect to a cumulative frequency of circle-equivalent diameters, and an average roundness in a range of from about 0.5 to about 0.85, wherein:

about 95% or more, by number of particles, of the primary particles satisfy the following Formula (1) with respect to a roundness (R) and a particle diameter (D) (nm):

$$R=\alpha \times D/1000+\beta \qquad \text{Formula (1)}$$

$(-1.9 \leq \alpha \leq -0.9, 0.82 \leq \beta \leq 1.11)$, the average roundness is a 50% cumulative frequency of a roundness of 100 primary particles as obtained by image analysis using the following Formula (2):

$$R=4\pi \times (A/I^2) \qquad \text{Formula (2)}$$

where R represents the roundness of a primary particle in an image, I represents a perimeter of the primary particle in the image, and A represents a projected area of the primary particle in the image, and a surface of the silica particles is hydrophobized with an organosilicon compound comprising a trimethylsilyl group, the organosilicon compound being at least one selected from the group consisting of a silazane compound and a silane compound.

2. The silica particles according to claim 1, wherein the organosilicon compound comprising a trimethylsilyl group comprises a trimethylmethoxysilane or a hexamethyldisilazane.

3. The silica particles according to claim 1, wherein an added amount of the organosilicon compound is in a range of from about 1% by weight to about 100% by weight with respect to an amount of the silica particles.

4. The silica particles according to claim 1, wherein an added amount of the organosilicon compound is in a range of from about 5% by weight to about 80% by weight with respect to an amount of the silica particles.

5. A method for producing the silica particles according to claim 1, the method comprising:

providing an alkali catalyst solution, which includes a first alkali catalyst at a concentration of from about 0.6 mol/L to about 0.85 mol/L, in a solvent comprising an alcohol; and supplying tetraalkoxysilane and a second alkali catalyst to the alkali catalyst solution;

the tetraalkoxysilane being supplied at a supply rate of from about 0.006 mol/(mol·min) to about 0.009 mol/(mol·min) with respect to 1 mol of the alcohol in the alkali catalyst solution; and the second alkali catalyst being supplied in an amount of from about 0.1 mol to about 0.4 mol per minute with respect to 1 mol of a total supply amount of the tetraalkoxysilane supplied per minute.

6. The method for producing the silica particles according to claim 5, wherein the solvent comprising the alcohol is an alcohol or a mixed solvent comprising the alcohol and at least one solvent selected from the group consisting of water, ketones, ethylene glycol monoethers, monoesters of ethylene glycol monoethers, and ethers.

7. The method for producing the silica particles according to claim 6, wherein an amount of the alcohol with respect to the at least one solvent is about 80% by weight or more.

8. The method for producing the silica particles according to claim 5, wherein the first alkali catalyst is at least one selected from the group consisting of ammonia, urea, monoamines, and a quaternary ammonium salt.

9. The method for producing the silica particles according to claim 5, wherein the tetraalkoxysilane is at least one selected from the group consisting of tetramethoxysilane, tetraethoxysilane, tetrapropoxysilane and tetrabutoxysilane.

10. The method for producing the silica particles according to claim 5, wherein the supply rate of the tetraalkoxysilane with respect to an amount by mol of the alcohol in the alkali catalyst solution is from about 0.0065 mol/(mol·min) to about 0.0085 mol/(mol·min).

* * * * *